(12) United States Patent
Yamamoto (10) Patent No.: US 11,457,798 B2
(45) Date of Patent: Oct. 4, 2022

(54) SMALL-DIAMETER ENDOSCOPE SURGICAL INSTRUMENT

(71) Applicant: Hidehiro Yamamoto, Hyogo (JP)

(72) Inventor: Hidehiro Yamamoto, Hyogo (JP)

( * ) Notice: Subject to any disclaimer, the term of this patent is extended or adjusted under 35 U.S.C. 154(b) by 468 days.

(21) Appl. No.: 16/322,187

(22) PCT Filed: Jul. 24, 2017

(86) PCT No.: PCT/JP2017/026598
§ 371 (c)(1),
(2) Date: Jan. 31, 2019

(87) PCT Pub. No.: WO2018/025680
PCT Pub. Date: Feb. 8, 2018

(65) Prior Publication Data
US 2019/0183320 A1 Jun. 20, 2019

(30) Foreign Application Priority Data
Aug. 2, 2016 (JP) .............................. JP2016-151724

(51) Int. Cl.
*A61B 1/01* (2006.01)
*A61B 1/00* (2006.01)
(Continued)

(52) U.S. Cl.
CPC ............ *A61B 1/01* (2013.01); *A61B 1/00087* (2013.01); *A61B 1/00135* (2013.01);
(Continued)

(58) Field of Classification Search
CPC ... A61B 1/00087; A61B 1/01; A61B 1/00154; A61B 1/00135
See application file for complete search history.

(56) References Cited

U.S. PATENT DOCUMENTS 5,478,329 A * 12/1995 Ternamian ......... A61B 17/3421
604/274
5,578,053 A * 11/1996 Yoon .................. A61B 10/0233
606/165

(Continued)

FOREIGN PATENT DOCUMENTS

| DE | 3313325 | 10/1984 |
|---|---|---|
| JP | 2007-089690 | 4/2005 |
| JP | 2014-018299 | 2/2014 |

OTHER PUBLICATIONS

Needlescopic Surgery for Palmar Hyperhidrosis, Yamamoto et al., The Journal of Thoracic and Cardiovascular Surgery, vol. 120, pp. 276-279 (2000).

*Primary Examiner* — Matthew J Kasztejna
(74) *Attorney, Agent, or Firm* — Simpson & Simpson, PLLC (57) ABSTRACT

This small-diameter endoscope surgical instrument comprises: an inner pipe 20 that has an outer diameter equal to that of a small-diameter endoscope 10 to be used, that is used for inserting the small-diameter endoscope surgical instrument into a body, and that is replaced with the small-diameter endoscope 10 after insertion thereof; a guide pipe 30 which is configured to have the small-diameter endoscope or the inner pipe inserted therethrough and which supports the small-diameter endoscope or the inner pipe so as to be movable in an axial direction; and a treatment pipe 40 which is configured to have the guide pipe inserted therethrough to support the guide pipe so as to be movable in the axial direction, and which has, at the leading end thereof, a treatment means such as an electrode, a blade, or a hook, wherein each of the small-diameter endoscope, inner pipe, guide pipe, and treatment pipe has an independent operation part at the proximate end thereof, and thus the rotation angle and the position in the axial direction thereof can be changed. The present invention enables, with a simple configuration, gripping or fixing of tissues, electrocautery, electrocoagulation, ablation, mobilization, separation, or traction of tissues, and further enables removal of blood clots, etc., stuck to a hook during surgery, and a sample extraction for biopsy.

15 Claims, 9 Drawing Sheets

(51) Int. Cl.
*A61M 3/02* (2006.01)
*A61B 18/14* (2006.01)

(52) U.S. Cl.
CPC .......... *A61B 1/00154* (2013.01); *A61B 18/14* (2013.01); *A61M 3/02* (2013.01); *A61B 1/0008* (2013.01)

(56) References Cited

U.S. PATENT DOCUMENTS

| | | | | |
|---|---|---|---|---|
| 5,776,112 | A * | 7/1998 | Stephens | A61B 17/3496 604/164.01 |
| 6,001,084 | A * | 12/1999 | Riek | A61B 17/3496 600/101 |
| 6,428,539 | B1 * | 8/2002 | Baxter | A61B 18/1482 606/49 |
| 6,585,638 | B1 | 7/2003 | Yamamoto | |
| 7,556,633 | B2 * | 7/2009 | Lindsay | A61B 17/00008 606/190 |
| 8,531,064 | B2 * | 9/2013 | Robertson | A61B 17/320068 310/50 |
| 2003/0009085 | A1 * | 1/2003 | Arai | A61B 1/00089 600/127 |
| 2005/0288622 | A1 * | 12/2005 | Albrecht | A61B 17/3417 604/23 |
| 2007/0083081 | A1 | 4/2007 | Schlagenhauf | |
| 2007/0203395 | A1 * | 8/2007 | Mikkaichi | A61B 1/00089 600/129 |
| 2016/0367279 | A1 * | 12/2016 | Orphanos | A61B 1/00082 |

\* cited by examiner

FIG. 9

SMALL-DIAMETER ENDOSCOPE SURGICAL INSTRUMENT

TECHNICAL FIELD

The present invention relates to an endoscope surgical instrument. The endoscope surgical instrument is used in surgery to perform abscission, mobilization (an act to move tissue), separation, attraction, extraction, electrocautery, electrocoagulation, etc. of small tissue in a body cavity, such as thoracic sympathectomy.

DESCRIPTION OF THE BACKGROUND

Surgery using an endoscope is called endoscopic surgery. In endoscopic surgery, surgical instruments, such as a scalpel, forceps, an electrode for coagulation, are used to be inserted in a body cavity through another skin incision different from a skin incision for an endoscope. Therefore, at least two skin incisions are required, and depending on a kind of the operation, it is necessary to provide skin incisions more than three places. However, fewer and smaller skin incisions are desirable, in order to reduce a surgical damage on a patient and to make fast postoperative recovery. In the following explanations, this type of instruments used in endoscopic surgery are called "conventional endoscope surgical instruments".

PTL 1 shows an endoscope power supplying appliance, having a cylinder unit which includes an endoscope in its inside. It can be inserted through a single skin incision into a body cavity and perform an operation, such as electrocautery, electrocoagulation, incision, etc. while observing a surgical area with the endoscope. It is an instrument to solve the above-mentioned issues of the conventional endoscope surgical instruments. The endoscope power supplying appliance perform electrocautery or electrocoagulation, using the leading end of the cylinder unit as an electrode and the cylinder unit itself as power supply unit. Also, the endoscope power supplying appliance can perform incision, etc., using the leading end of the cylinder unit which is formed in a blade or a needle shape.

The cylinder unit of the endoscope power supplying appliance has an inner diameter which allows the endoscope to move in its inside, and the endoscope is supported so as to be movable in the axial direction of the cylinder unit. Then, a relative position in their axial direction of the leading end of the cylinder unit and the leading end of the endoscope becomes variable. At the time of searching the target point of the operation, the endoscope is projected over the leading end of the cylinder unit so as to observe in the body cavity with a wide visual field, and at the time of the operation, the endoscope is pulled into the cylinder unit and the endoscope can focus on both of the target point of the operation and the leading end of the treatment mean, such as electrode. Using this endoscope power supplying appliance, the endoscope and the surgical instruments are inserted as an unity into the body cavity through only one skin incision, and a further skin incision is not required.

Details and results of an operation using this endoscope power supplying appliance are shown in NPL 1.

PTL 2 shows an endoscope power supplying appliance suitable for sympathicotomy, which can attract, move, or cut fiber organization interfering with an endoscope's view, by adding an attraction mean to the endoscope power supplying appliance according to PTL 1.

The endoscope power supplying appliances shown in PTL 1 or PTL 2 need only a single skin incision. Also, a size of the skin incision can be made smaller, as those endoscope power supplying appliances use small-diameter endoscopes. It contributes to reduce a surgical damage on patient and to make fast postoperative recovery.

However, these endoscope power supplying appliances cannot grip or fix tissue. Therefore, they cannot detach tissue entangled in a blade or remove a blood clot stuck on a blade during an incision operation, without pulling out these endoscope power supplying appliances themselves from a body cavity. Also, they are not able to grip and extract an incised tissue from the body cavity, as a sample for a biopsy.

With the conventional endoscope surgical instruments, an operator can insert a grasper, such as forceps, to grip tissue, or to extract an incised tissue as a sample for a biopsy from the body cavity. But, to do so, additional skin incision is required for inserting a grasper, such as forceps. An ordinary-used remote control grasper, such as remote control forceps, has a large number of small parts, such as a joint pin and driving mechanisms to move the grasping hands relatively. Those parts may be broken and fallen apart within a body cavity. Incidentally, an existence of the fallen-apart small parts can be confirmed by radiography from the outside of the body. But, as it is difficult to detect the exact position of the fallen-apart parts even with an endoscope, it is almost impossible to take out those fallen-apart small parts from a body, even using endoscope surgical instruments.

In addition to those issues, many of the conventional endoscope surgical instruments have leading ends with a sharp or a complicated shape. When they are inserted in a body, it may damage the neighboring tissue, or the leading end of the endoscope surgical instrument itself may be damaged, and the insertion cannot be performed smoothly. Also, during the insertion, it is rather difficult for the operator to judge up to where the leading end of the endoscope surgical instrument have arrived.

CITATION LIST

Patent Literature

[PTL 1] WO-A1-2000/016707
[PTL 2] JP-A1-2007/089690

Non-Patent Literature

[NPL 1] Hidehiro Yamamoto, MD. etc. The Journal of Thoracic and Cardiovascular Surgery, 2000, Volume 120, Page 276-279

SUMMARY OF INVENTION

[Technical Object]

In response to the above issues, the present invention provides an endoscope surgical instrument which discharges functions to grip and fix tissue, additional to the functions of the endoscope power supplying appliances shown in PLT 1 or PLT 2. Consequently, it can detach tissue entangled in a blade and remove a blood clot stuck on a blade during an incision operation, and it can grip and extract an incised tissue from the body cavity as a sample for a biopsy. Also, the endoscope surgical instrument can be inserted in a body smoothly, and do not damage the neighboring tissue or the leading end of the endoscope surgical instrument itself. And during the insertion, an operator can judge easily, up to where the leading end of the endoscope surgical instrument has arrived. Of course, with an endoscope included in the endoscope surgical instrument, it is essential to obtain a clear view, on both of the surgery target point and treatment mean, such as an electrode etc. and a clear view on the surrounding area around the leading end of the endoscope surgical instrument.

Solution to Technical Object

A small-diameter endoscope surgical instrument according to a first aspect of the present invention is of coaxial and multiplex-pipe structure, includes a small-diameter endoscope, an inner pipe, a guide pipe, a treatment pipe and their operation handles. The inner pipe has an outside diameter same as the one of a pipe part of the small-diameter endoscope, and is used when the small-diameter endoscope surgical instrument is inserted into a body, and replaced with the small-diameter endoscope after the insertion. The guide pipe, in which the small-diameter endoscope or the inner pipe is inserted, supports them so as to be movable in their axial direction. The treatment pipe, in which the guide pipe is inserted and supported so as to be movable in their axial direction, has one or more treatment means, such as an electrode, a blade, a hook, etc., at its leading end. The operation handles, independently included to the small-diameter endoscope, the inner pipe, the guide pipe, and the treatment pipe, at their each proximate end, that is an end locating outside of a body of a patient being operated with the small-diameter endoscope surgical instrument. Those operation handles can change their positions in their axial direction and some of their rotating angles.

The following description is on thoracic sympathectomy, as an example. When the small-diameter endoscope surgical instrument is introduced into a thoracic cavity through a single skin incision made in an armpit of a patient, the inner pipe which has an outside diameter same as the one of a pipe part of the small-diameter endoscope is inserted in the guide pipe, and the guide pipe is inserted in the treatment pipe. Therefore, the small-diameter endoscope surgical instrument is of coaxial and triple-pipe structure. After confirming the distal end of the small-diameter endoscope surgical instrument has reached to the target point, the inner pipe is replaced with the small-diameter endoscope. As a result, whole items required to an endoscopic operation are inserted in a body cavity through only one skin incision.

Surgical instruments inserted into a body, such as an endoscope surgical instrument, used to be in a shape of a pole which is filled up with a material, and not in a shape of a pipe. If the surgical instrument is in a pipe shape, a part of tissue or body fluid enters into an inside of the pipe. In this case, it is hard to prevent pollution of such a surgical instrument and to sterilize it thoroughly. One aspect of the present invention is the small-diameter endoscope surgical instrument of multiplex-pipe structure. When it is inserted into a body, it is of triple-pipe structure. When it is in an operation, it is of double-pipe structure plus a small-diameter endoscope. By decreasing a difference between an outer diameter of the small-diameter endoscope or the inner pipe and an inner diameter of the guide pipe, and by decreasing a difference between an outer diameter of the guide pipe and an inner diameter of the treatment pipe, to be minimal, under a condition that each items are supported so as to be movable in their axial direction, it gives a minimal possibility that a part of tissue or body fluid enters into the clearances of the small-diameter endoscope surgical instrument, as explained in the description of embodiments. As the inner pipe, the guide pipe and the treatment pipe have a shape of simple pipe, and also they are easy to be separated each other, washing and sterilization of them can be performed easily and thoroughly.

The small-diameter endoscope surgical instrument has a small outside diameter, by selecting an endoscope which has a pipe part of a very small outside diameter, the inner pipe has a same outside diameter, and the guide pipe and the treatment pipe with thin pipe walls. Consequently, the small skin incision is enough to insert it into a body.

When an operator inserts the small-diameter endoscope surgical instrument into a body cavity, leading ends of the inner pipe, the guide pipe and the treatment pipe are slightly shifted to their operation handle side in this order. Each of those components has a shape of simple pipe and has no part projecting outside of the pipe part of the treatment pipe, the operator can insert it in a body cavity very smoothly.

The small-diameter endoscope, the inner pipe, the guide pipe and the treatment pipe independently include operation handles, at their proximate end. An operator of the small-diameter endoscope surgical instrument may change their positions in their axial direction and their rotating angles, depending on a requirement. The treatment pipe requires to change its rotating angle. The guide pipe requires to change its rotating angle in order to change the small-diameter endoscope's view in case it has at least one slit. But the guide pipe without any slit does not require to change its rotating angle. The inner pipe does not require to change its rotating angle. The operation handles are provided, taking these conditions into consideration.

An operator can perform not only electrocautery and electrocoagulation of a tissue which is a target of the operation (it will be called "target tissue" hereunder), using the electrode at the leading end of the treatment pipe, but also abscission, mobilization, separation and attraction, using the blade, the hook, etc., at the leading end of the treatment pipe. Furthermore, using the hook at the distal end of the treatment pipe and a distal end of the guide pipe, the operator may grip a target tissue. Consequently, the operator may mobilize, separate and attract the target tissue, and also he may extract the gripped target tissue from a body cavity as a sample for a biopsy. Also, the operator may detach a tissue entangled in the blade or remove blood clots stuck on the blade, by fixing them between the leading end of the guide pipe and a rib, etc. The operator can perform these operations effectively and efficiently, managing an operation handle included to each component.

All components, that is the small-diameter endoscope, the inner pipe, the guide pipe, and the treatment pipe, are formed in a linear shape or in a part of an arc shape with a same radius, as they are to be changed their relative positions in their axial direction.

The small-diameter endoscope surgical instrument according to a second aspect of the present invention, may include a treatment pipe which has a special hook. The hook is formed by cutting out from the wall of the distal end of the treatment pipe, and a near edge of a tip of the hook has a blade and is in a plain approximately perpendicular to the axial direction of the treatment pipe.

"The hook is formed by cutting out from the wall of the treatment pipe" means a hook made by cutting out from the pipe wall of the treatment pipe, keeping a radius of the pipe wall as it was, and the hook part are located within the same inside and outside diameter as the treatment pipe itself. Consequently, the hook part does not disturb the relative movement between the treatment pipe and the guide pipe. Also, when the small-diameter endoscope surgical instrument is inserted into a body, the hook part does not damage a neighboring tissue, and a tip of the hook is not forced to be damaged, as the hook part accompanies the guide pipe, just like as the treatment pipe itself.

The hook has a shape that a pushing-out part from the leading end of the treatment pipe lengthens ahead and then turns to make the hook. A near edge, that is a side near to the operator, of a tip of the turning part of the hook are in a plain approximately perpendicular to the axial direction of the treatment pipe, and it is parallel to the leading end of the guide pipe which is formed perpendicular to its axial direction. An operator puts a target tissue between the near edge of a tip of the hook and the leading end of the guide pipe, and brings the near edge of a tip of the hook and the leading end of the guide pipe close each other by managing their operation handles. With this special hook, the operator grip the target tissue more easily and more tightly, than the case that a near edge of a tip of a hook is not parallel to a leading end of a guide pipe. Consequently, mobilization, separation, attraction of the target tissue and also a sample extraction for a biopsy can be performed more easily and more surely.

Providing a blade on the near edge of a tip of the hook, an operator can perform abscission and separation of a target tissue more easily and more surely, by pulling the operation pipe in and turning it, managing its operation handle.

When an operator wants to detach a tissue entangled in the blade or remove a blood clot stuck on the blade, he can detach or remove them very easily, by fixing them between the leading end of the guide pipe and a rib, etc., and then rotating the treatment pipe. With the small-diameter endoscope surgical instrument, an operator can detach or remove them easily without taking out the small-diameter endoscope surgical instrument itself from a body. It helps a smooth progress of operation and reduces surgical damage on patient. With a conventional endoscope surgical instrument, an operator cannot perform these operation, without pulling the conventional endoscope surgical instrument out from a body, in many cases.

The small-diameter endoscope is supported so as to be movable in its axial direction by the guide pipe, and the guide pipe is supported so as to be movable in its axial direction by the treatment pipe. When searching a target tissue, an operator can observe in a body cavity with a wide visual field, by pushing out the small-diameter endoscope from the leading ends of the guide pipe and the treatment pipe. In operation, the operator can focus on both a target tissue and the treatment mean of the leading end of the treatment pipe, by pulling the small-diameter endoscope into the guide pipe and the treatment pipe. In both cases, he can get clear view.

As the small-diameter endoscope, the guide pipe and the treatment pipe of the small-diameter endoscope surgical instrument are combined in coaxial, an operator can observe both a target tissue and a treatment mean, such as an electrode. In the conventional endoscope surgical instrument, the operator needs to make an effort searching a treatment mean in a body cavity with an endoscope, and chasing the treatment mean with the endoscope during whole operation period, so that the treatment mean is within the endoscope's view. With the small-diameter endoscope surgical instrument, an operator does not need such actions. It decreases an operator's burden and operation is performed more smoothly.

The small-diameter endoscope surgical instrument according to a third aspect of the present invention, may have a guide pipe, which includes one or more slits near its leading end. An operator can get a view around a target tissue through the slits, when the operator pulls the small-diameter endoscope into the guide pipe to perform an operation, such as grip, etc., and the leading end of the guide pipe narrows the endoscope's view. It is a great help for the operator.

The small-diameter endoscope surgical instrument according to a fourth aspect of the present invention, may include an treatment pipe, which has an electrode at its leading end and its pipe part supplies electricity to the electrode. An outer surface of the treatment pipe, being inserted into a body except the electrode, is insulated.

The treatment pipe is made of current-carrying material, and has an electrode for electrocautery or electrocoagulation at its leading end. A pipe part of the treatment pipe works as an electricity supplying wire. For preventing short-circuit to an outside, an outer surface of the treatment pipe being inserted into a body except the electrode, is insulated. The insulation is carried out by coating, printing or baking of insulating material. The electrode is either mono-polar or bipolar. Mono-polar electrode is suitable for a delicate operation, such as thoracic sympathectomy, as an electric current is concentrated in relatively small portion around the electrode.

The small-diameter endoscope surgical instrument according to a fifth aspect of the present invention, may include an inner pipe which has a leading end of a polished smooth round head and a physiological saline solution or air supplying equipment supplying them to an inside of the inner pipe.

During an insertion of the small-diameter endoscope surgical instrument into a body, the inner pipe is used as a replacement of the small-diameter endoscope, and leads the small-diameter endoscope surgical instrument. With a leading end of a polished smooth round head of the inner pipe, the insertion is performed smoothly.

A physiological saline solution or air supplying equipment, such as a syringe filled with physiological saline solution or air, is prepared. It is connected to the inner pipe with a flexible tube, to supply them to an inside of the inner pipe. For example, in case of sympathectomy, an operator can notice an advancing movement of a piston of the syringe, when the leading end of the inner pipe reached into a pleural cavity, as a pressure of the physiological saline solution or air falls down. The operator can judge easily up to where the leading end of the small-diameter endoscope surgical instrument reached.

Advantageous Effects of Invention

Using the small-diameter endoscope surgical instrument of the present invention, an operator can perform abscission, mobilization, separation, attraction, extraction, electrocautery, electrocoagulation, etc. for a small tissue in a body cavity, with only one instrument. Especially, he can detach a tissue entangled in a blade or remove a blood clot stuck on a blade at the operating place, and he can extract an incised tissue from a body cavity as a sample for a biopsy, as he can perform griping and fixing of a tissue easily and surely.

An operator does not bother about taking out of fallen parts in a body cavity, as the small-diameter endoscope surgical instrument is simple structure made of only a few components.

The small-diameter endoscope surgical instrument needs only one and small skin incision. It contributes to deduce surgical damage of the patient and early recovery of a postoperative stage.

An operator can insert the small-diameter endoscope surgical instrument in a body smoothly, and do not damage the neighboring tissue or the leading end of the small-diameter endoscope surgical instrument. During the insertion, he can judge easily up to where the leading end of the small-diameter endoscope surgical instrument has arrived. With a small-diameter endoscope inserted within the small-diameter endoscope surgical instrument, he can get a clear surgical view, on both of the surgery target point and treatment mean, such as the electrode etc. and on the surrounding area around the leading end of the small-diameter endoscope surgical instrument. The small-diameter endoscope surgical instrument is used easily and extremely handy for an operator.

NPL 1 presents an endoscope power supplying appliance which performs sympathectomy, sympathicotomy and ablation, such as electrocautery, to destroy sympathetic trunk. But it is hard to perform sympathetic ganglionectomy with this endoscope power supplying appliance, as sympathetic ganglions usually locate between ribs and contact with brood vessels in many cases. The use of the small-diameter endoscope surgical instrument of the present invention makes possible all of these operations. Also, it has a big advantage for a patient praying for low invasion and high cosmesis.

BRIEF DESCRIPTION OF DRAWINGS

FIG. 2 shows components which compose the small-diameter endoscope surgical instrument according to Embodiment 1 of the invention.

FIG. 4 shows a detail of the treatment pipe according to Embodiment 1 of the invention.

FIG. 5 shows operations using the hook of the treatment pipe according to Embodiment 1.

DESCRIPTION OF EMBODIMENTS

A small-diameter endoscope surgical instrument according to embodiments of the present invention will now be described with reference to the drawings. The present invention will not be limited only to these embodiments, and may include various changes on its structure within Claims. The following descriptions are on thoracic sympathectomy, but a use of the present invention is not limited to thoracic sympathectomy.

Embodiment 1

Figure 1A:
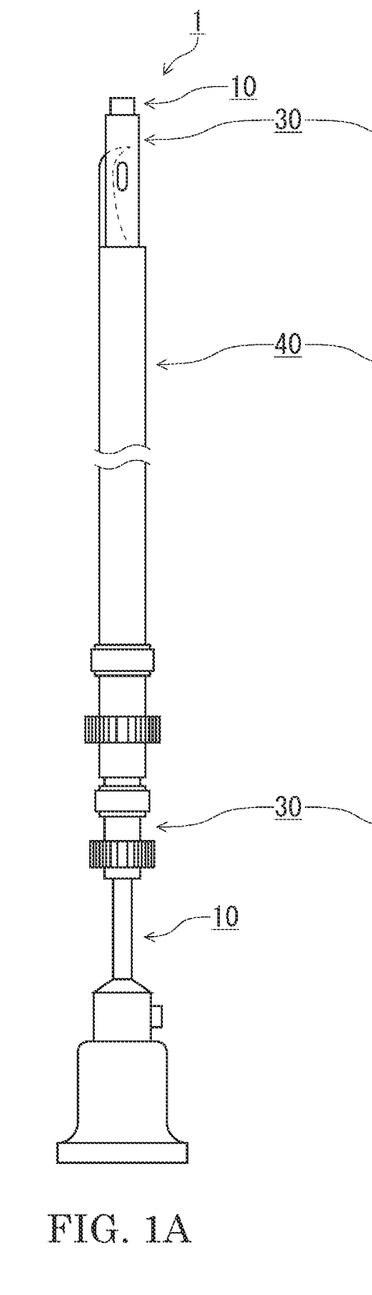
FIG. 1A is a perspective view of a small-diameter endoscope surgical instrument according to Embodiment 1 of the invention, during an operation.
Figure 1B:
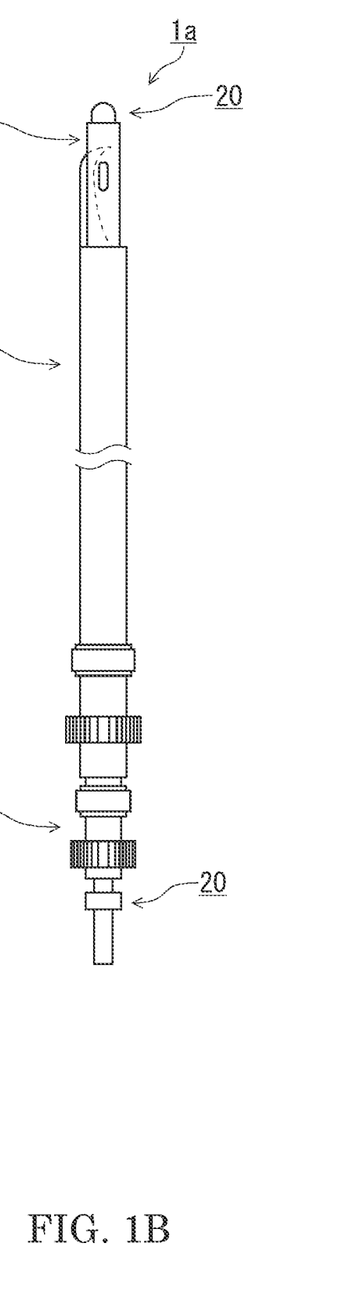
FIG. 1B is a perspective view of the same, during an insertion into a body.
Figure 2A:
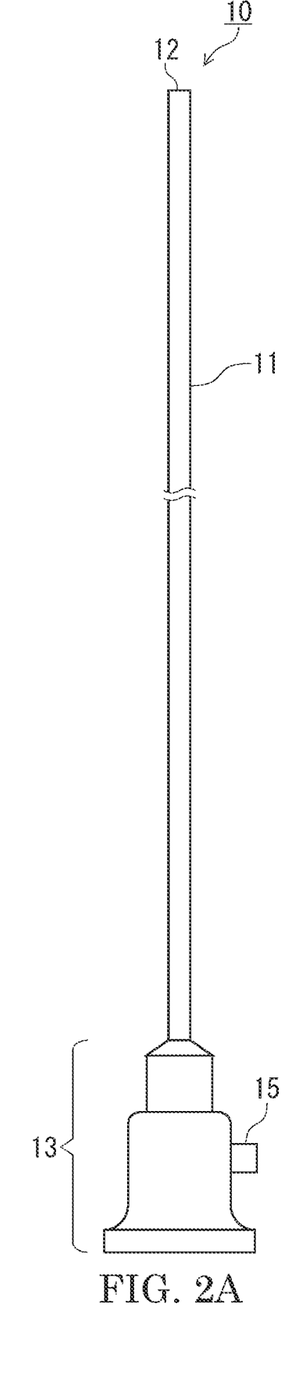
FIG. 2A is a perspective view of a small-diameter endoscope.
Figure 2B:
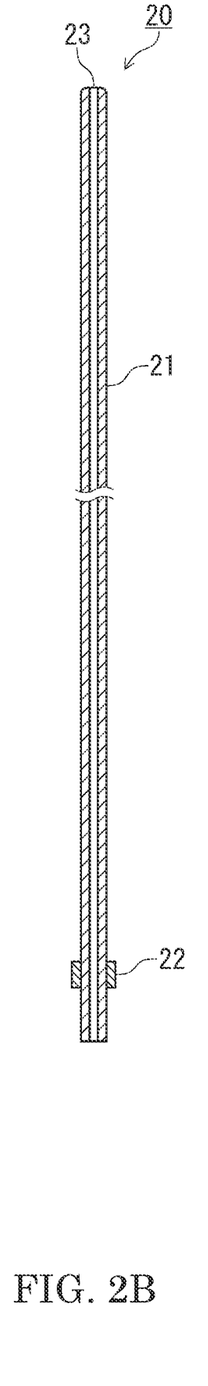
FIG. 2B is a sectional view of an inner pipe.
Figure 2C:
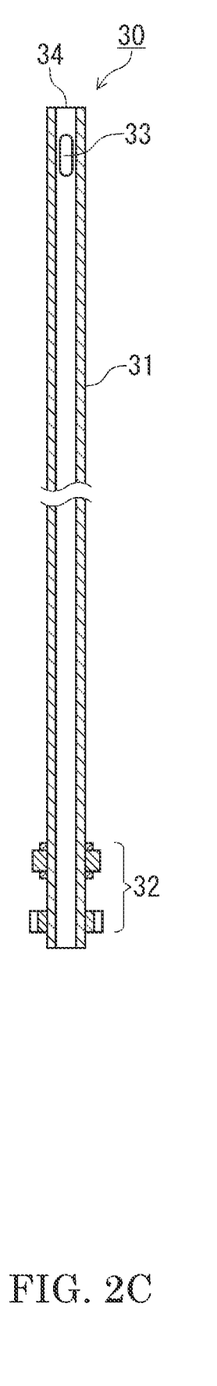
FIG. 2C is a sectional view of a guide pipe. And, FIG. 2D is a sectional view of a treatment pipe.
Figure 2D:
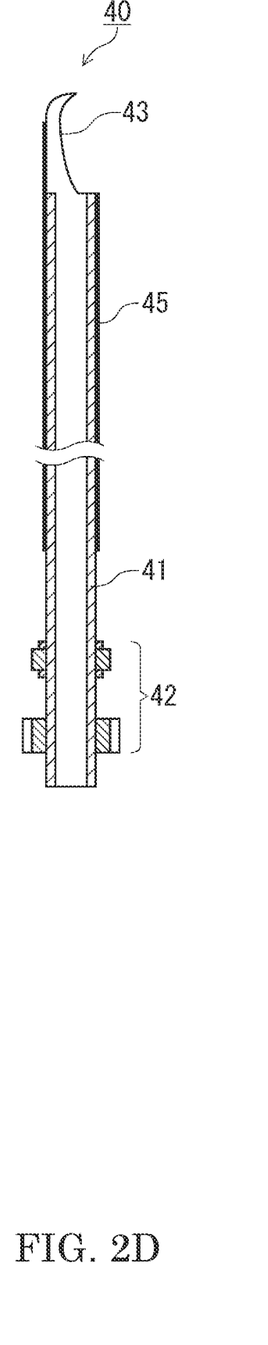
Figure 3:
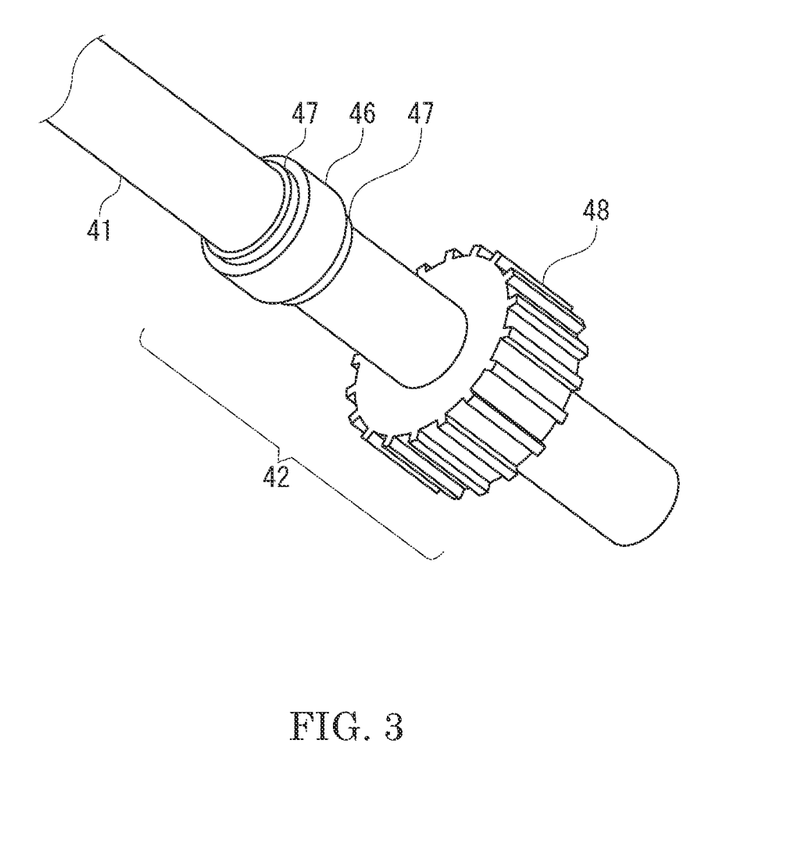
FIG. 3 is an explanatory diagram of a handle of the treatment pipe according to Embodiment 1 of the invention.
Figure 4A:
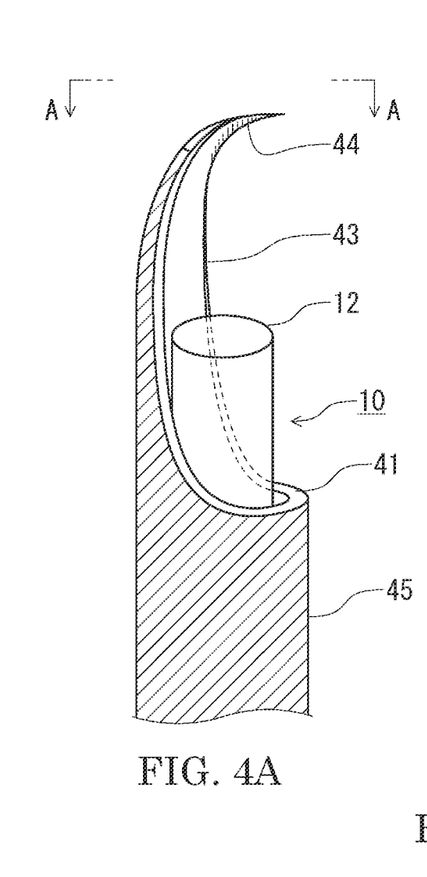
FIG. 4A is an explanatory diagram of a hook provided at a leading end of the treatment pipe.
Figure 4B:
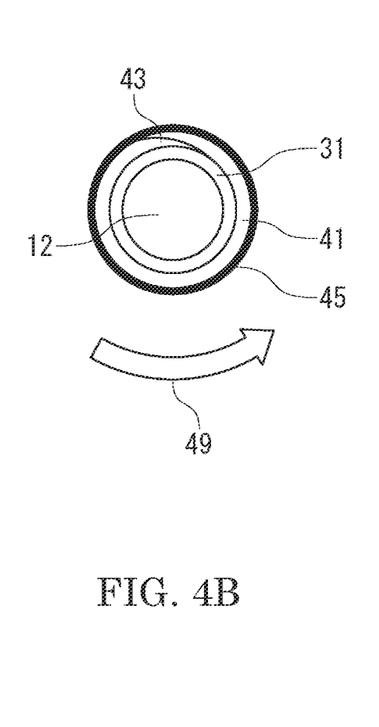
FIG. 4B is its A-A view.

FIG. 1A is a perspective view of a small-diameter endoscope surgical instrument according to Embodiment 1 of the invention, during an operation. FIG. 1B is a perspective view of the same, during an insertion into a body. FIG. 2 shows components which compose the small-diameter endoscope surgical instrument according to Embodiment 1 of the invention. FIG. 2A is a perspective view of a small-diameter endoscope. FIG. 2B is a sectional view of an inner pipe. FIG. 2C is a sectional view of a guide pipe. And, FIG. 2D is a sectional view of a treatment pipe. FIG. 3 is an explanatory diagram of a handle of the treatment pipe according to Embodiment 1 of the invention. FIG. 4 shows a detail of the treatment pipe according to Embodiment 1 of the invention. FIG. 4A is an explanatory diagram of a hook provided at a leading end of the treatment pipe. FIG. 4B is its A-A view.

A small-diameter endoscope surgical instrument 1 according to Embodiment 1 of the present invention during an operation, includes a small-diameter endoscope 10, a guide pipe 30, and a treatment pipe 40, as shown in FIG. 1A. The small-diameter endoscope surgical instrument 1a during its insertion into a body, replace the small-diameter endoscope with an inner pipe 20. It is in coaxial and triple-pipe structure. To minimize the size of a skin incision, the small-diameter endoscope 10 of this embodiment includes a rigid fiberscope in a pipe part 11. An outside diameter of the rigid fiberscope is 2 mm.

The small-diameter endoscope 10 is led to a standard endoscopic monitor system (It is not shown in a figure) by a connector 13, and an operator proceed an operation watching a surgical target area and its around through the endoscopic monitor. An optical fiber for illumination to light up a neighboring space around a leading end 12 of the small-diameter endoscope is included in the pipe part 11 and light is sent through a light fiber connector 15. An operator uses the connector 13 as a handle of the small-diameter endoscope, and moves the leading end of the small-diameter endoscope instrument to a surgical target point.

A guide pipe 30 is a pipe with an inside diameter 2.05 mm, which is slightly bigger than the outside diameter of the pipe part 11 of the small-diameter endoscope, and it has an outside diameter 2.35 mm. The guide pipe 30 supports the small-diameter endoscope 10 so as to be movable in its axial direction. In a case that one or more slits 33 are provided at a leading end 34 of the guide pipe, it may help an operator to get a view around the surgical target area and remove quickly white smoke in the front of the small-diameter endoscope 10, when the small-diameter endoscope is pulled into the guide pipe 30.

A treatment pipe 40 is a pipe with an inside diameter 2.40 mm, which is slightly bigger than the outside diameter 2.35 mm of the guide pipe 30, and supports the guide pipe so as to be movable in its axial direction. All components of the small-diameter endoscope surgical instrument 1a inserted into a body, are within the treatment pipe. The treatment pipe 40 is a simple pipe without any project-aside portion. It can be inserted smoothly through a skin incision of approximately 3 mm in length.

The treatment pipe 40 includes a hook 43 at its leading end. The hook 43 is made by cutting out from a wall of the treatment pipe into a hook shape, without any transformation on a curved surface of the treatment pipe wall. Consequently, the hook 43 is located between curved inside and outside surfaces, which has the same inside and outside diameter of the treatment pipe wall. Therefore, the hook 43 does not disturb an axial movement of guide pipe 30 in the treatment pipe 40, and not project aside from the outer diameter of the treatment pipe 40.

Many conventional endoscope surgical instruments may include a leading end with a sharp hook or a sharp blade. When they are inserted in a body, it may damage the neighboring tissue, or the leading end of the instruments may be damaged, and the insertion cannot be performed smoothly. As the hook 43 has the shape as shown in FIG. 4A and FIG. 4B, and it advances accompanying the guide pipe 30 when it is inserted in a body, it does not damage the neighboring tissue, and does not be damaged.

A near edge, that is a side near to the operation handle, of a tip 44 of the hook 43 is parallel to the leading end 34 of the guide pipe 30, which is formed perpendicular to its axial direction. As the near edge of the tip 44 of the hook is parallel to the leading end 34 of the guide pipe, an operator can grip a tissue tightly, by managing handles 42 and 32 and bringing the near edge of the tip 34 close to the leading end 34 of the guide pipe.

With a blade provided at the near edge of the tip 44 of the hook 43, the operator can perform abscission or separation of a target tissue very easily and surely, by pulling and turning the treatment pipe 40 to a direction 49 in FIG. 4B. During this operation, the operator pulls the leading end 12 of the small-diameter endoscope 10 into the treatment pipe 40, and can get a clear view of both the blade of the tip 44 and a target tissue, as shown in FIG. 4A. In this occasion, the guide pipe 30 is pulled in the treatment pipe 40, in order not to interfere with the view.

The tip 44 of the hook 43 is used as a blade, and also as an electrode for electrocautery or electrocoagulation. A pipe part 41 of the treatment pipe is made of current-carrying material and works as an electricity supplying wire itself.

For preventing short-circuit to an outside, an outer surface of the treatment pipe being inserted into a body except the electrode, is insulated.

The insulation 45 is carried out by coating, printing or baking of insulating material. The electrode is either mono-polar or bipolar. Mono-polar electrode is suitable for a delicate operation on a small tissue in a body cavity, such as thoracic sympathectomy, as an electric current is concentrated in relatively small portion around the electrode. When the tip 44 is used as a mono-polar electrode, another electrode may be provided at a part of patient's body, such as a buttock.

The treatment pipe 40 includes a handle 42 at its operator's near side, as shown in FIG. 3. The handle 42 includes a rotator 48, a hold 46 and snap rings 47. The rotator 48 is fixed to the pipe part 41 of the treatment pipe. The hold 46 is put on the pipe part 41 so as to be rotatable, but not removable in the treatment pipe's axial direction by the snap rings 47 fixed to the pipe part 41. The operator pinches the hold 46 with his thumb and forefinger and touches the rotator 48 with his middle finger. He can change the axial position of the treatment pipe 40 by moving the hold 46, and can change the rotating angle of the treatment pipe 40 by rotating the rotator 48.

A guide pipe 30 may have at least one slit, as shown in FIG. 2B. The slit gives an operator a view around a leading end 34 of the guide pipe, and the operator can change a direction of the view by rotating the guide pipe. In this case, the guide pipe 30 needs a handle 32, which is similar to the handle 42 of the treatment pipe. A guide pipe without any slit, does not needs to rotate itself and to have a rotator. It has only a hold fixed to the pipe part of the guide pipe.

The inner pipe 20 is a pipe which has a same outside diameter as a one of a pipe part 11 of the small-diameter endoscope. Its leading end 23 works as a leader of the small-diameter endoscope surgical instrument 1a, when it is inserted into a body, as shown in FIG. 1B. The leading end 23 may be in polished smooth round head, in order to be inserted smoothly and not to injure a neighboring tissue. The inner pipe 20 needs to change its axial position but does not need to rotate itself. Therefore, it does not need a rotator, and needs only a hold 22 fixed to the pipe part 21 of the inner pipe. The hold 22 has a shape easily pinched with operator's thumb and forefinger.

Each of the inner pipe 20, the guide pipe 30, and the treatment pipe 40 have minimal diameter and minimal wall thickness, under the condition that each component can perform its function. The clearances between those pipes are selected small. Consequently, a diameter of the pipe part of the small-diameter endoscope instrument 1 according to Embodiment 1 of this invention, is only 2.85 mm. It contributes to reduce a size of a skin incision for its insertion. Also, by decreasing a difference between an outer diameter and an inner diameter of pipes being close to each other, that is a clearance between pipes being close to each other, it gives a minimal possibility that a part of tissue or a body fluid enters into the appliance.

As the inner pipe 20, the guide pipe 30 and the treatment pipe 40 are in simple pipe form, and they are easy to be separated each other, washing and sterilization of them can be performed easily and thoroughly.

Figure 5A:
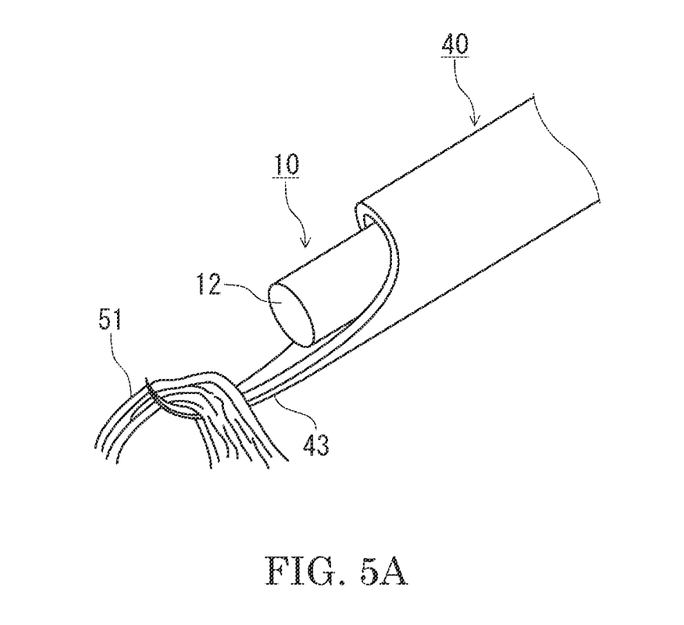
FIG. 5A is an explanatory diagram of mobilization.

FIG. 5A is an explanatory diagram of an operation to move a tissue (mobilization), using the hook 43 of the treatment pipe. In some operations, an operator may want to remove a tissue which interferes with the small-diameter endoscope surgical instrument's advance or the small-diameter endoscope's view. In such a case, the operator puts the hook 43 of the treatment pipe close to the interfering tissue 51, managing the hold 46 and watching the hook 43 and the interfering tissue 51 with the small-diameter endoscope 10. Then, he manages the rotator 48 to change an angle of the hook 43, and hooks the interfering tissue 51. Under this situation, he can perform mobilization, isolation and attraction of the interfering tissue 51, and he can also perform abscission of it, using the blade on the hook 43.

Figure 5B:
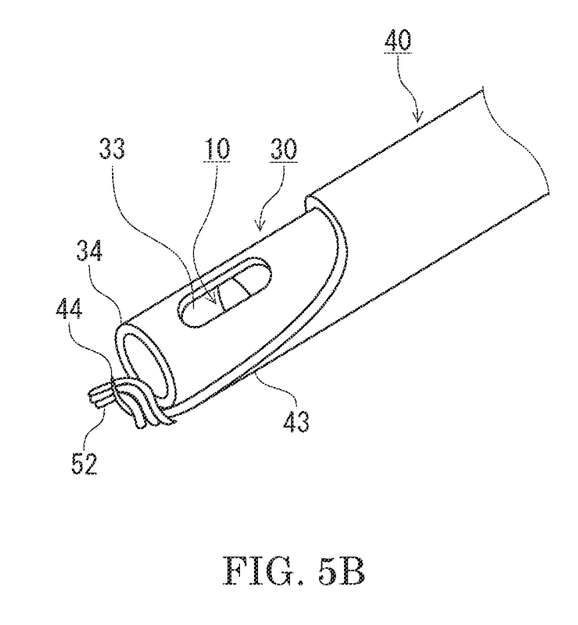
FIG. 5B is an explanatory diagram of griping.

FIG. 5B is an explanatory diagram of an operation to grip a tissue. An operator puts the hook 43 of the treatment pipe close to a target tissue 52, managing the hold 46 and watching the hook 43 and the target tissue 52 with the small-diameter endoscope 10. Then, he manages the rotator 48 to change an angle of the hook 43, and hooks the target tissue 52, just like as mobilization. Then, he moves the guide pipe 30 ahead, managing the handle 32 and grips the hooked tissue 52 between a leading end 34 of the guide pipe and a tip 44 of the hook 43. The slit 33 on the guide pipe helps him to get a small-diameter endoscope's view, when the guide pipe 30 has moved ahead.

The tip 44 of the hook 43 curves, so that a near edge of the tip is parallel to the leading end 34 of the guide pipe 30. The operator can grip the tissue 52 tightly between the near edge of the tip 44 of the hook and the leading end 34 of the guide pipe, and he can perform mobilization, isolation and attraction of the tissue 52. Also, the tissue 52 can be used for biopsy, by pulling the small-diameter endoscope surgical instrument 1 gripping the tissue 52, out from the body.

Figure 6:
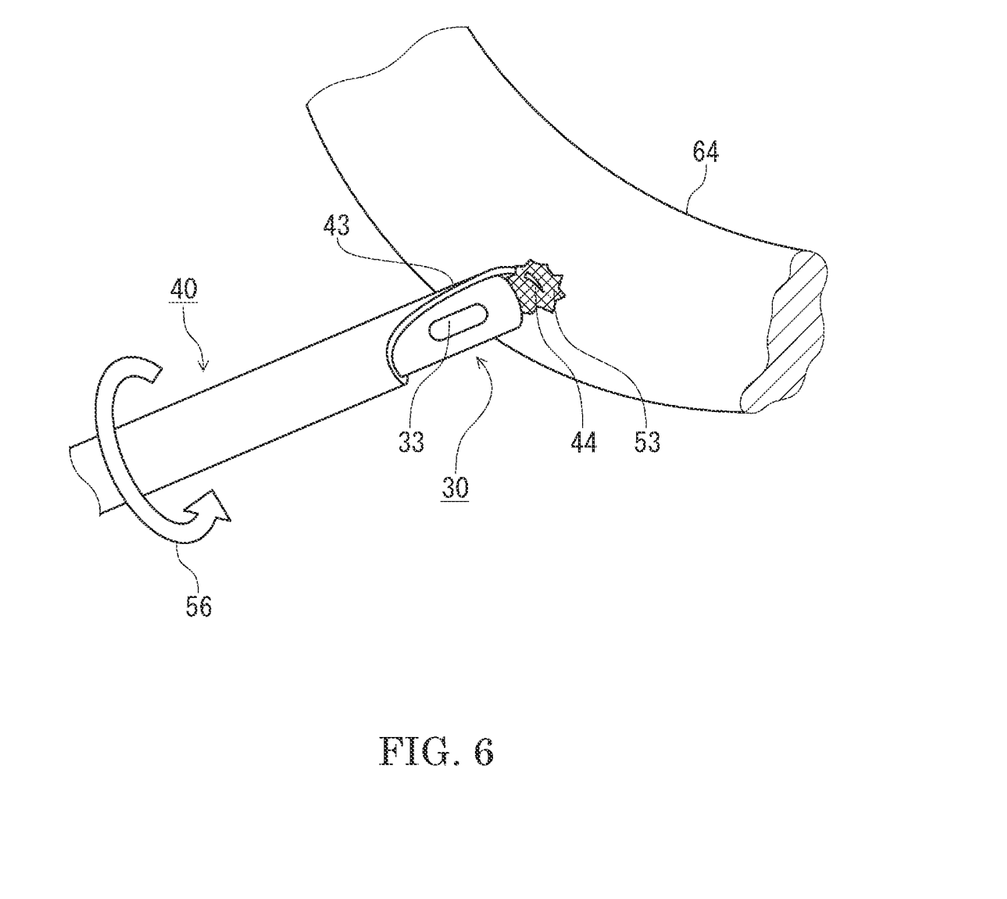
FIG. 6 is an explanatory diagram of an operation to fix and detach a tissue entangled in a blade or remove a blood clot stuck on a blade, using the guide pipe.

FIG. 6 is an explanatory diagram of an operation to fix and detach a tissue 53 entangled in a tip 44 of a hook 43 or remove a blood clot stuck on a blade. An operator searches for a rigid object, such as a rib 64, using a small-diameter endoscope, and brings a hook 43 of the treatment pipe close to the rib 64, managing a handle 42 of the treatment pipe. Then, he moves the guide pipe 30 ahead, managing the handle 32 of the guide pipe, and fixes the tissue 53 or the blood clot, by pushing them on the rib. Under this situation, he may take the tissue 53 or the blood clot off from the hook 43 easily, by turning the treatment pipe 40 in an arrow 56 shown in FIG. 6, managing the rotator 48.

Entanglement with a tissue and sticking with a blood clot happened many times during an operation. At that time, an operator had to take an endoscope surgical instrument out from a body every time, to detach an entangled tissue or to remove a stuck blood clot from a hook. Using the small-diameter endoscope surgical instrument according to this Embodiment, he can detach the entangled tissue or remove the stuck blood clot, without taking the small-diameter endoscope surgical instrument out from a body. It helps a smooth progress of an operation and reduces surgical damage on a patient.

Figure 7:
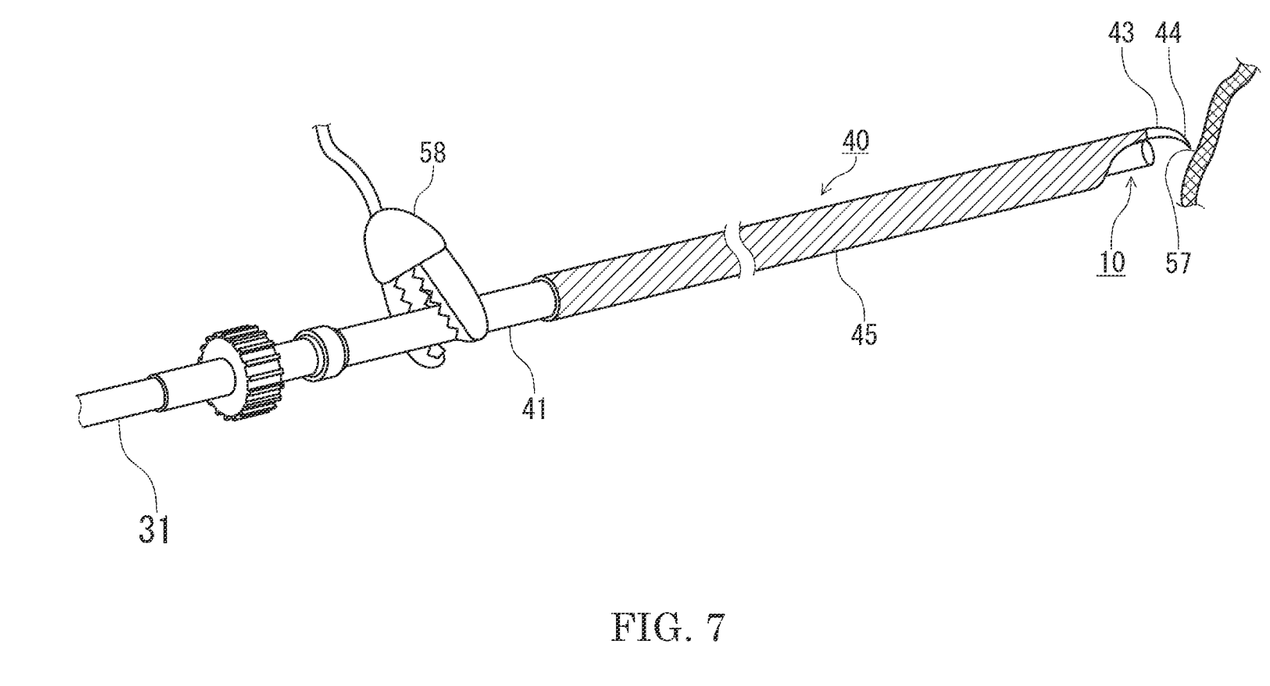
FIG. 7 is an explanatory diagram of electrocautery or electrocoagulation, using an electrode of the treatment pipe.

FIG. 7 is an explanatory diagram of electrocautery or electrocoagulation, using an electrode of a treatment pipe. An operator puts a crocodile clip on a non-insulated pipe part 41 of the treatment pipe 40, for supplying a power. Also, he puts an electrode on a buttock of the patient, which is not shown on the figure. With such an arrangement, he can perform electrocautery or electrocoagulation on a target tissue 57. He can get a small-diameter endoscope's view including both the electrode (a tip 44 of a hook) and a target tissue 57, without any interference by a guide pipe because the guide pipe is pulled into the treatment pipe 40.

Embodiment 2

Figure 8:
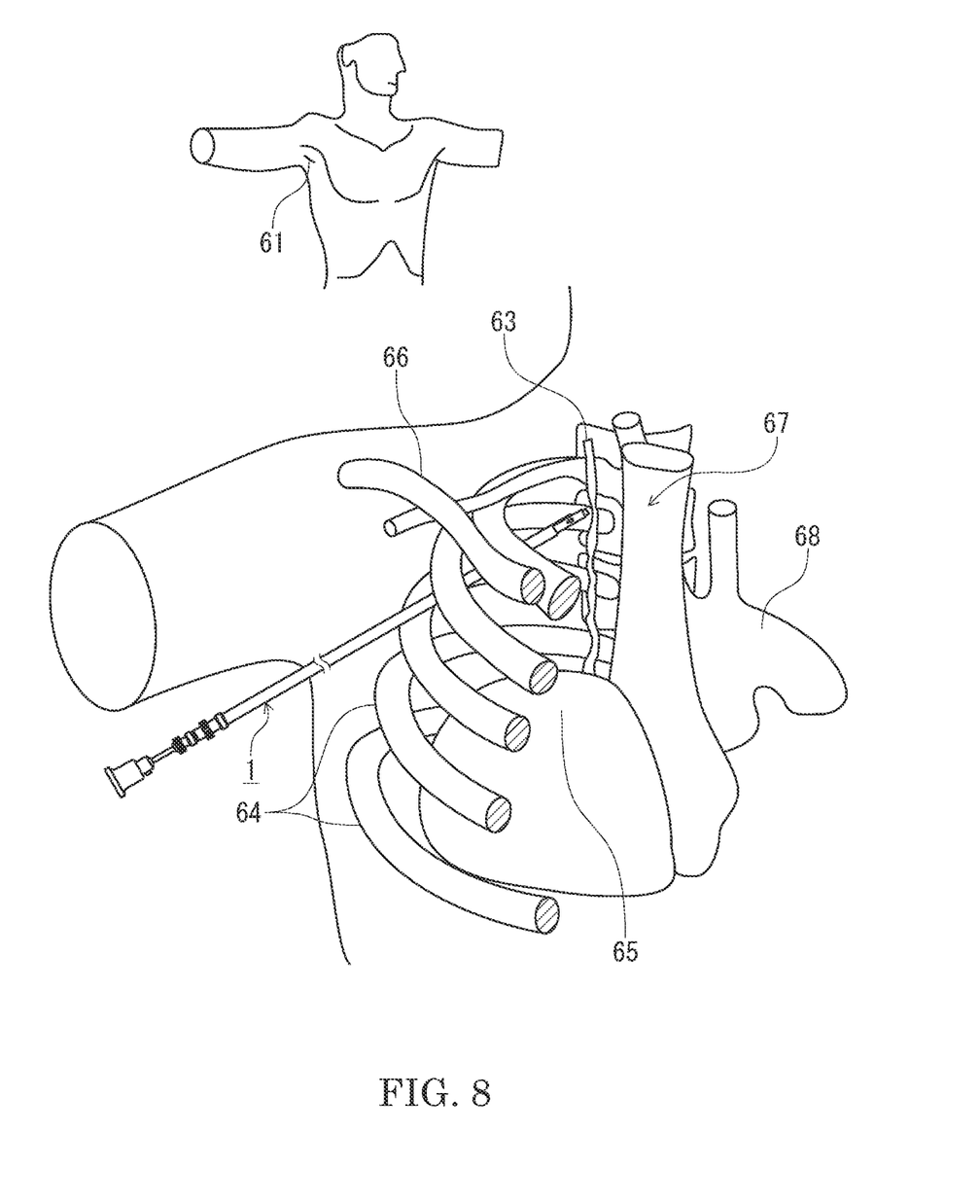
FIG. 8 is an explanatory diagram of insertion of the small-diameter endoscope surgical instrument according to Embodiment 1 of the invention (Embodiment 2). (This diagram is quoted from J Thoracic Cardiovasc Surg. 2000; 120: 276-9.)
Figure 9:
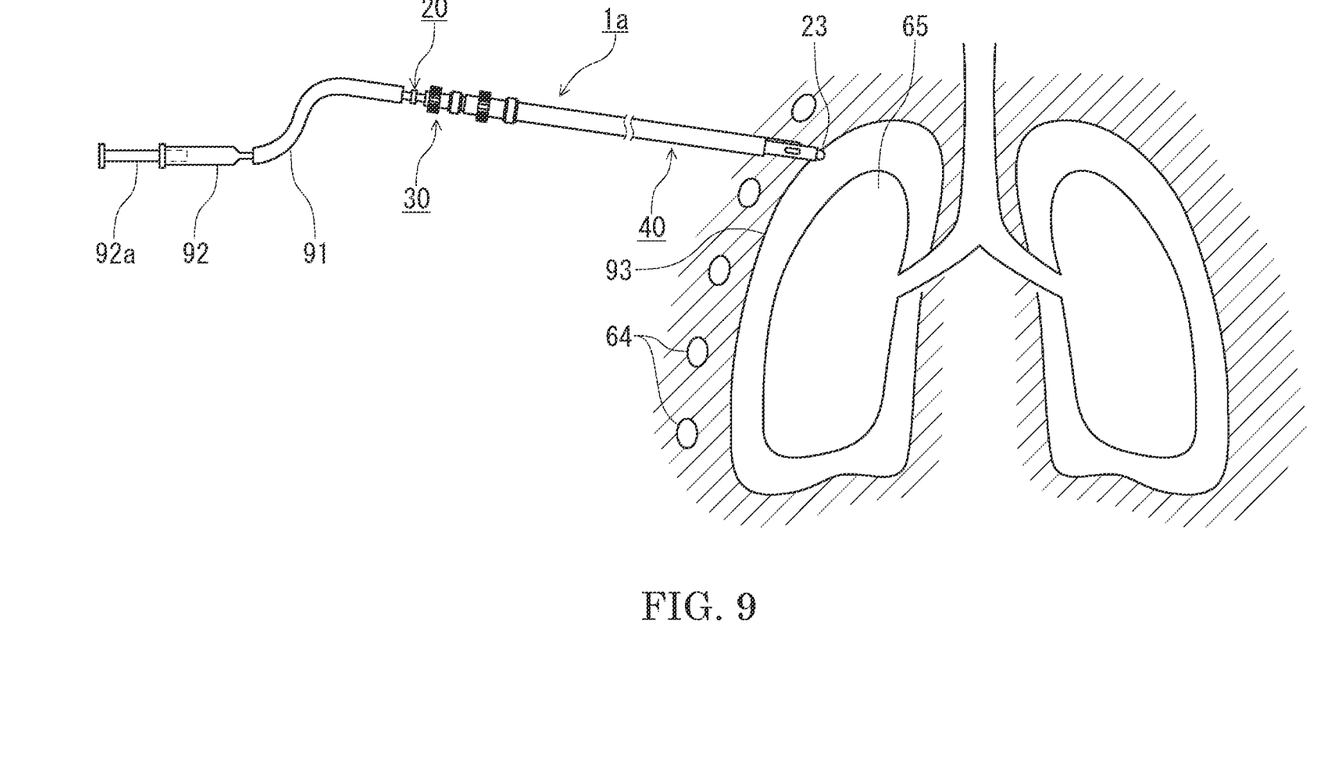
FIG. 9 is an explanatory diagram of judging up to where the leading end of the small-diameter endoscope surgical instrument has reached, according to Embodiment 2 of the invention.

FIG. 8 is an explanatory diagram of insertion of the small-diameter endoscope surgical instrument according to Embodiment 1 of the invention. (This diagram is quoted from J Thoracic Cardiovasc Surg. 2000; 120: 276-9.) FIG. 9 is an explanatory diagram of judging up to where the leading end of the small-diameter endoscope surgical instrument has reached, according to Embodiment 2 of the invention.

An operator makes a skin incision 61 with a length 3 mm on an armpit of a patient, to perform thoracic sympathectomy using a small-diameter endoscope surgical instrument according to Embodiment 1. The operator inserts the small-diameter endoscope surgical instrument 1a, which has an inner pipe 20 substituted for a small-diameter endoscope 10, through the skin incision 61 into a thoracic cavity. A target tissue of this operation is a thoracic sympathetic trunk 63 placed along a backbone. The small-diameter endoscope surgical instrument 1a advances through a space between ribs 64, to reach near the target tissue 63. The area is surrounded with an apex of a lung 65, a clavicle 66, a super vena cava 67 and an aorta 68, besides the ribs 64.

The inner pipe 20 of the small-diameter endoscope surgical instrument 1a is connected to a syringe 92 with a flexible tube 91. The syringe 92 includes physiological saline solution or air. When the leading end of the small-diameter endoscope surgical instrument 1a, that is the leading end 23 of the inner pipe 20 reaches a pleural cavity, a pressure of physiological saline solution or air decreases, as a pressure in the pleural cavity is in a negative pressure. And a piston 92a of the syringe 92 moves ahead. An operator can notice the advance movement of a piston 92a, and judges easily and with confidence, the arrival of the leading end of the small-diameter endoscope surgical instrument 1a to the pleural cavity 93.

After this judgement, he takes out the inner pipe 20 from the small-diameter endoscope surgical instrument 1a, and inserts a small-diameter endoscope 10 as a substitution of the inner pipe. It changes the small-diameter endoscope surgical instrument 1a into a small-diameter endoscope surgical instrument 1 during an operation.

INDUSTRIAL APPLICABILITY

The small-diameter endoscope surgical instrument of the invention has a simple structure with a few components, even so, it discharges many functions. It can perform electrocautery, electrocoagulation, abscission, mobilization, separation, attraction of a target tissue. Also, it can perform mobilization, separation and attraction of a target tissue, by griping or fixing the tissue. Moreover, it can take out a tissue as a sample for biopsy, and it can detach an entangled tissue or remove a blood clot from the hook, without taking the small-diameter endoscope surgical instrument out of the body cavity. Using the small-diameter endoscope surgical instrument, an operator can perform an operation smoothly with an easy action, watching a small-diameter endoscope's clear view. For a patient, only one small skin incision reduces surgical damage. With those advantages, the small-diameter endoscope surgical instrument is expected to be used in more various operations in the future.

REFERENCE SIGNS LIST 1, 1a A small-diameter endoscope surgical instrument of Embodiment 1
10 A small-diameter endoscope
11 A pipe part of the small-diameter endoscope
12 A leading end of the small-diameter endoscope
13 A connector (a handle) of the small-diameter endoscope
15 A light fiber connecter of the small-diameter endoscope
20 An inner pipe
21 A pipe part of the inner pipe
22 A handle of the inner pipe
23 A leading end of the inner pipe
30 A guide pipe
31 A pipe part of the guide pipe
32 A handle of the guide pipe
33 A slit of the guide pipe
34 A leading end of the guide pipe
40 A treatment pipe
41 A pipe part of the treatment pipe
42 A handle of the treatment pipe
43 A hook of the treatment pipe
44 A tip of the hook of the treatment pipe
45 An insulation on the treatment pipe
46 A hold of the treatment pipe
47 Snap rings of the treatment pipe
48 A rotator of the treatment pipe
49, 56 A rotating direction of the treatment pipe
51, 52, 57 Tissue
53 Blood clot
58 A crocodile clip
61 A skin incision
63 A thoracic sympathetic trunk
64 A rib
65 An apex of a lung
66 A clavicle
67 A superior vena cava 68 An aorta
91 A flexible tube
92, 92a A syringe
93 A pleural cavity

The invention claimed is:

1. A small-diameter endoscope surgical instrument system of coaxial and multiplex-pipe structure, comprising:
 a guide pipe having an inner diameter and an outer diameter, the guide pipe having a proximate end including at least one operation handle and a distal treatment end;
 an endoscope having an outer diameter smaller than the inner diameter of the guide pipe such that the endoscope is coaxially slidably receivable within the guide pipe, the endoscope having a proximate end including at least one operation handle and a distal treatment end, the endoscope and the guide pipe configured for axial and rotational movement relative to one another;
 an inner pipe having an outer diameter smaller than the inner diameter of the guide pipe such that the inner pipe is coaxially slidably receivable within the guide pipe, the inner pipe having a proximate end including at least one operation handle and a distal treatment end, the inner pipe and the guide pipe configured for axial movement relative to one another; and,
 a treatment pipe having a smooth, non-threaded outer wall and an inner diameter larger than the outer diameter of the guide pipe such that the guide pipe is coaxially slidably receivable within the treatment pipe, the treatment pipe having a proximate end including at least one operation handle and a distal treatment end, the treatment pipe and the guide pipe configured for axial and rotational movement relative to one another;
 wherein the treatment pipe is a cylindrical pipe and includes a hook, the hook having a shape formed by cutting out a portion
 of the cylindrical pipe such that the hook has a cylindrical tubular shape with the same inside and outside diameters, and the same central axis as the cylindrical pipe, the shape of the hook extending from the cylindrical pipe and curving along the cylindrical tubular shape toward a tip pointing in a tangential direction of the tubular shape; and,
 wherein, axial and rotational adjustment of the guide pipe, the endoscope or the inner pipe, and the treatment pipe relative to another may be provided by applying an axially or rotationally directed force upon a respective one of the at least one operation handle of one or more of the guide pipe, the endoscope or the inner pipe, and the treatment pipe.

2. The small-diameter endoscope surgical instrument system according to claim 1, wherein the treatment pipe includes an electrical insulator extending along an axial length of the treatment pipe and about the outer diameter of the treatment pipe, the treatment pipe including an exposed portion at its distal treatment end thereby forming an electrode capable of receiving a current.

3. The small-diameter endoscope surgical instrument system according to claim 1,
 wherein the distal treatment end of the inner pipe comprises a polished smooth round head; and
 the inner pipe includes a bore configured to pass a gas or liquid therethrough.

4. The small-diameter endoscope surgical instrument system according to claim 3, wherein the liquid is a physiological saline solution.

5. The small-diameter endoscope surgical instrument system according to claim 1,
 wherein the guide pipe has a first opening at its proximate end and a second opening at its distal treatment end, the first and second openings configured to allow any one of the distal treatment ends of the endoscope and the inner pipe to pass therethrough in a longitudinal direction of the guide pipe,
 wherein the guide pipe has at least one aperture disposed proximate its distal treatment end formed by boring the guide pipe wall in a radial direction of the guide pipe, and,
 the second opening and the aperture providing a simultaneous two-way view from the endoscope, the two-way view including a first view of the hook of the treatment pipe through the second opening and a second view of outside of the guide pipe through the aperture.

6. The small-diameter endoscope surgical instrument system according to claim 1, wherein the outer diameter of the endoscope is larger than an inner diameter of the inner pipe and substantially the same as the outer diameter of the inner pipe.

7. The small-diameter endoscope surgical instrument system according to claim 6, wherein the outer diameter of the endoscope and the outer diameter of the inner pipe are approximately 2 mm.

8. The small-diameter endoscope surgical instrument system according to claim 6, wherein, in a procedure wherein the small-diameter endoscope surgical instrument system is to be inserted into a body:
 the inner pipe is inserted into the guide pipe; and,
 upon insertion of the small-diameter endoscope surgical instrument system including the inner pipe, the inner pipe is replaced with the endoscope.

9. The small-diameter endoscope surgical instrument system according to claim 6, wherein the inner diameter of the guide pipe is approximately 2.05 mm and the outer diameter of the guide pipe is approximately 2.35 mm.

10. The small-diameter endoscope surgical instrument system according to claim 6, wherein the inner diameter of the treatment pipe is approximately 2.40 mm and the outer diameter of the treatment pipe is less than 3 mm.

11. The small-diameter endoscope surgical instrument system of claim 1, wherein the hook of the treatment pipe includes a base portion and a tip portion, the base portion having a width greater than the width of the tip portion, wherein an arcuate edge extends from the base portion to the tip portion, and wherein a portion of the arcuate edge includes the beveled knife edge, the beveled knife edge operatively arranged to perform a progressive slicing operation when the treatment pipe is one or more of pulled in a direction toward the proximate end thereof, turned or rotated, or combinations thereof.

12. The small-diameter endoscope surgical instrument system of claim 1, wherein in a case where the treatment pipe is utilized along with the guide pipe and a tissue or blood clot is entangled upon the tip of the hook of the treatment pipe, the tissue or blood clot is removable from the treatment pipe by placing the tissue or blood clot such that it abuts a rigid object, and applying an axially directed force upon the guide pipe in a direction of the distal end in order to fix the tissue or blood clot against the rigid object, and applying a rotational force upon the treatment pipe in a suitable direction such that the tissue or blood clot is taken off the hook or tip.

13. A small-diameter endoscope surgical instrument system of coaxial and multiplex-pipe structure, comprising:
- a guide pipe having an inner diameter and an outer diameter, the guide pipe having a proximate end including at least one operation handle and a distal treatment end;
- an endoscope having an outer diameter smaller than the inner diameter of the guide pipe such that the endoscope is coaxially slidably receivable within the guide pipe, the endoscope having a proximate end including at least one operation handle and a distal treatment end, the endoscope and the guide pipe configured for axial and rotational movement relative to one another;
- an inner pipe having an outer diameter smaller than the inner diameter of the guide pipe such that the inner pipe is coaxially slidably receivable within the guide pipe, the inner pipe having a proximate end including at least one operation handle and a distal treatment end, the inner pipe and the guide pipe configured for axial movement relative to one another; and,
- a treatment pipe having a smooth, non-threaded outer wall and an inner diameter larger than the outer diameter of the guide pipe such that the guide pipe is coaxially slidably receivable within the treatment pipe, the treatment pipe having a proximate end including at least one operation handle and a distal treatment end, the treatment pipe and the guide pipe configured for axial and rotational movement relative to one another;
- wherein, axial and rotational adjustment of the guide pipe, the endoscope or the inner pipe, and the treatment pipe relative to another may be provided by applying an axially or rotationally directed force upon a respective one of the at least one operation handle of one or more of the guide pipe, the endoscope or the inner pipe, and the treatment pipe;
- wherein the guide pipe has a first opening at its proximate end and a second opening at its distal treatment end, the first and second openings configured to allow any one of the distal treatment ends of the endoscope and the inner pipe to pass therethrough in a longitudinal direction of the guide pipe,
- the guide pipe has at least one aperture disposed proximate its distal treatment end formed by boring the guide pipe wall in a radial direction of the guide pipe, and,
- the second opening and the aperture provide a simultaneous two-way view from the endoscope, the two-way view including a first view of the hook of the treatment pipe through the second opening and a second view of outside of the guide pipe through the aperture.

14. The small-diameter endoscope surgical instrument system of claim 13, wherein the hook of the treatment pipe includes a base portion and a tip portion, the base portion having a width greater than the width of the tip portion, wherein an arcuate edge extends from the base portion to the tip portion, and wherein a portion of the arcuate edge includes the beveled knife edge, the beveled knife edge operatively arranged to perform a progressive slicing operation when the treatment pipe is pulled in a direction toward the proximate end thereof, turned or rotated, or combinations thereof.

15. The small-diameter endoscope surgical instrument system of claim 13, wherein in a case where the treatment pipe is utilized along with the guide pipe and a tissue or blood clot is entangled upon the tip of the hook of the treatment pipe, the tissue or blood clot is removable from the treatment pipe by placing the tissue or blood clot such that it abuts a rigid object, and applying an axially directed force upon the guide pipe in a direction of the distal end in order to fix the tissue or blood clot against the rigid object, and applying a rotational force upon the treatment pipe in a suitable direction such that the tissue or blood clot is taken off the hook or tip.

* * * * *